US012731671B2

(12) United States Patent
Kiani

(10) Patent No.: US 12,731,671 B2
(45) Date of Patent: Sep. 8, 2026

(54) INDIVIDUALIZED MEAL KIT WITH REAL-TIME FEEDBACK AND CONTINUOUS ADJUSTMENTS BASED ON LIFESTYLE TRACKING

(71) Applicant: Cercacor Laboratories, Inc., Irvine, CA (US)

(72) Inventor: Massi Joe E. Kiani, Laguna Niguel, CA (US)

(73) Assignee: Willow Laboratories, Inc., Irvine, CA (US)

(*) Notice: Subject to any disclaimer, the term of this patent is extended or adjusted under 35 U.S.C. 154(b) by 160 days.

(21) Appl. No.: 17/831,135

(22) Filed: Jun. 2, 2022

(65) Prior Publication Data

US 2022/0392610 A1 Dec. 8, 2022

Related U.S. Application Data

(60) Provisional application No. 63/196,532, filed on Jun. 3, 2021.

(51) Int. Cl.
*G16H 20/60* (2018.01)

(52) U.S. Cl.
CPC .................................. *G16H 20/60* (2018.01)

(58) Field of Classification Search
CPC ..................................................... G16H 20/60
See application file for complete search history.

(56) References Cited

U.S. PATENT DOCUMENTS 4,960,128 A 10/1990 Gordon et al.
4,964,408 A 10/1990 Hink et al.
5,319,355 A 6/1994 Russek
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage et al.
5,431,170 A 7/1995 Mathews
(Continued)

FOREIGN PATENT DOCUMENTS

CN 104303185 A * 1/2015 .......... A61B 5/4866
CN 104376203 A * 2/2015
(Continued)

OTHER PUBLICATIONS

US 2022/0192529 A1, 06/2022, Al-Ali et al. (withdrawn)
(Continued)

*Primary Examiner* — Kenneth Bartley
(74) *Attorney, Agent, or Firm* — Knobbe, Martens, Olson & Bear, LLP

(57) ABSTRACT

The present disclosure describes example systems, methods, and computer-readable medium for dynamic meal planning. A meal planning system can include one or more processors configured to obtain exercise data, meal data, health data, user preference data, and/or other data; determine a health score based at least in part on the exercise data and/or the meal data; generate a user-specific meal kit based at least in part on the exercise data, the meal data, the health data, the user preference data, the other data and/or the health score; and communicate an indication of the user-specific meal kit.

13 Claims, 4 Drawing Sheets

(56) References Cited

U.S. PATENT DOCUMENTS 5,436,499 A 7/1995 Namavar et al.
D361,840 S 8/1995 Savage et al.
D362,063 S 9/1995 Savage et al.
D363,120 S 10/1995 Savage et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,561,275 A 10/1996 Savage et al.
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,128 A * 3/1999 Diaz .................... G16H 20/30 705/2
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin, IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.

(56) References Cited

U.S. PATENT DOCUMENTS

D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,183,498 B2 * 11/2015 Landers ................ G16H 20/30
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,364,106 B1 * 6/2016 Ortiz ...................... B65D 25/04
9,392,945 B2 7/2016 Al-Ali et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,622,692 B2 4/2017 Lamego et al.
D788,312 S 5/2017 Al-Ali et al.
9,649,054 B2 5/2017 Lamego et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.
9,955,937 B2 5/2018 Telfort
9,965,946 B2 5/2018 Al-Ali et al.
D820,865 S 6/2018 Muhsin et al.

(56) References Cited

U.S. PATENT DOCUMENTS

| | | | |
|---|---|---|---|
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |

(56) References Cited

U.S. PATENT DOCUMENTS

D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 * 10/2024 Pauley .................. G16H 40/67
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.
12,478,272 B2 11/2025 Telfort et al.
12,478,293 B1 11/2025 Al-Ali et al.
D1,106,466 S 12/2025 Avendaño et al.
12,495,967 B2 12/2025 Muhsin et al.
12,495,999 B2 12/2025 Al-Ali et al.
12,507,952 B2 12/2025 Al-Ali et al.
12,521,021 B2 1/2026 Al-Ali et al.
12,521,506 B2 1/2026 Yu et al.
12,538,084 B1 1/2026 Telfort et al.
12,539,046 B2 2/2026 Kiani
12,575,797 B2 3/2026 Olsen et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2005/0240444 A1 * 10/2005 Wooten .................. G06Q 30/02
705/3
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0137297 A1 6/2011 Kiani et al.
2011/0172498 A1 7/2011 Olsen et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0041591 A1 2/2013 Lamego
2013/0060147 A1 3/2013 Welch et al.
2013/0096405 A1 4/2013 Garfio
2013/0157232 A1 * 6/2013 Ehrenkranz ............ G16H 20/60
206/459.1
2013/0296672 A1 11/2013 O'Neil et al.
2013/0345921 A1 12/2013 Al-Ali et al.
2014/0166076 A1 6/2014 Kiani et al.
2014/0180160 A1 6/2014 Brown et al.
2014/0187973 A1 7/2014 Brown et al.
2014/0258208 A1 * 9/2014 Landers ................. G06N 5/048
706/52
2014/0275871 A1 9/2014 Lamego et al.
2014/0275872 A1 9/2014 Merritt et al.
2014/0287384 A1 * 9/2014 Boyes ...................... G09B 5/02
434/127
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0058263 A1 * 2/2015 Landers ................. G06N 20/00
706/11
2015/0073241 A1 3/2015 Lamego

(56) References Cited

U.S. PATENT DOCUMENTS

2015/0080754 A1 3/2015 Purdon et al.
2015/0099950 A1 4/2015 Al-Ali et al.
2015/0194071 A1* 7/2015 Bennett .................. G16H 20/30 434/127
2015/0289810 A1* 10/2015 Pacione ................. A61B 5/165 600/300
2015/0339949 A1* 11/2015 Landers ................. G16H 40/63 434/127
2015/0364057 A1* 12/2015 Catani .................... G16H 10/60 434/262
2016/0196388 A1 7/2016 Lamego
2016/0252390 A1* 9/2016 Batsikouras ........... G01G 23/36 177/25.13
2016/0367173 A1 12/2016 Dalvi et al.
2017/0024748 A1 1/2017 Haider
2017/0173632 A1 6/2017 Al-Ali
2017/0251974 A1 9/2017 Shreim et al.
2018/0211723 A1* 7/2018 Coles ..................... G16H 20/60
2018/0233064 A1* 8/2018 Dunn ................. G09B 19/0092
2018/0242926 A1 8/2018 Muhsin et al.
2018/0247712 A1 8/2018 Muhsin et al.
2019/0239787 A1 8/2019 Pauley et al.
2019/0320906 A1 10/2019 Olsen
2019/0374713 A1 12/2019 Kiani et al.
2020/0043596 A1* 2/2020 Koretoff ................ G16H 50/30
2020/0060869 A1 2/2020 Telfort et al.
2020/0111552 A1 4/2020 Ahmed
2020/0113435 A1 4/2020 Muhsin
2020/0113496 A1 4/2020 Scruggs et al.
2020/0113520 A1 4/2020 Abdul-Hafiz et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1* 4/2021 Pauley ................... G16H 20/60
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0183493 A1* 6/2021 Oh ....................... A61B 5/7267
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0386382 A1 12/2021 Olsen et al.
2021/0402110 A1 12/2021 Pauley et al.
2022/0005580 A1* 1/2022 Pavlov ................... A61B 5/486
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0167916 A1* 6/2022 Mohanty .............. A61B 5/6823
2022/0172820 A1* 6/2022 Neumann .............. G06N 20/00
2022/0218244 A1 7/2022 Kiani et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Al-Ali
2023/0058342 A1 2/2023 Kiani
2023/0058760 A1* 2/2023 Ishigaki ................. G16H 20/60
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0255764 A1 8/2025 Stead
2025/0278512 A1 9/2025 Koo et al.
2025/0281059 A1 9/2025 Avendano
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.
2025/0318761 A1 10/2025 Al-Ali et al.
2025/0322950 A1 10/2025 Al-Ali et al.
2025/0323417 A1 10/2025 Rey
2025/0329240 A1 10/2025 Kiani
2025/0344010 A1 11/2025 Al-Ali et al.
2026/0014333 A1 1/2026 Fernkvist et al.
2026/0014334 A1 1/2026 Danwihl
2026/0048198 A1 2/2026 Vo et al.

FOREIGN PATENT DOCUMENTS

CN 110689455 A * 1/2020 ............. G06F 21/32
CN 111009306 A * 4/2020
WO WO-0205702 A2 * 1/2002 ........... A61B 5/0002
WO WO-2013123416 A2 * 8/2013 ........... A61B 5/4866
WO WO-2014087252 A2 * 6/2014 ............. G16H 10/20

(56) References Cited

FOREIGN PATENT DOCUMENTS

| | | | | | |
|---|---|---|---|---|---|
| WO | WO-2014113005 | A2 | * | 7/2014 | ......... G06F 19/3475 |
| WO | WO-2015179868 | A2 | * | 11/2015 | ............. G16H 10/20 |
| WO | WO-2021026399 | A1 | * | 2/2021 | ........... A61B 5/1118 |

OTHER PUBLICATIONS

CN-110689455, Lu et al., An Intelligent Dinner and Intelligent Tray System, Jan. 14, 2020, pp. 1-28 (Year: 2020).*

Chen et al., "Using e-Plate to Implement a Custom Dietary Management System," 2014, 2014 International Symposium on Computer, Consumer and Control, pp. 978-981. (Year: 2014).*

* cited by examiner

INDIVIDUALIZED MEAL KIT WITH REAL-TIME FEEDBACK AND CONTINUOUS ADJUSTMENTS BASED ON LIFESTYLE TRACKING

BACKGROUND

Making healthy choices is the key to weight management, fitness, wellness, disease prevention, and boosting immune system.

SUMMARY OF EMBODIMENT S

The systems, methods, and devices of this disclosure each have several innovative aspects, no single one of which is solely responsible for all of the desirable attributes disclosed herein.

The present disclosure describes example systems, methods, and computer-readable medium for dynamic meal planning. A meal planning system can include one or more processors configured to obtain exercise data, meal data, health data, user preference data, and/or other data; determine a health score based at least in part on the exercise data and/or the meal data; generate a user-specific meal kit based at least in part on the exercise data, the meal data, the health data, the user preference data, the other data and/or the health score; and communicate an indication of the user-specific meal kit.

The meal planning system of the preceding paragraph may also include any combination of the following features described in this paragraph, among others described herein. The one or more processors can be configured to obtain information relating to daily food and beverage intake, activity, physiological parameters. The one or more processors can be configured to obtain information relating to underlying health conditions, allergies, age, weight, historic meal logging, fitness goals, family customizations/info, etc. The one or more processors can be configured to generate a nutrition and exercise score (sometimes referred to as a health score) based on meal inputs and exercise inputs. The user-specific meal kit can be generated based on real-time feedback and/or continuous adjustments.

The meal planning system can include one or more processors configured to receive a scan of a menu or recipe, process the scan to identify one or more meals and/or ingredients of the one or more meals, select at least one of the one or more meals as a suggested meal, and outputting an indication of the suggested meal to the user.

The meal planning system of any of the preceding paragraphs may also include any combination of the following features described in this paragraph, among others described herein. The suggested meal may be a meal that fits within dietary needs, for example to achieve a particular daily, weekly, or meal score. The suggested meal may be a meal that has a highest health score, as compared to other meals of the menu. To process the scan, the one or more processors can be further configured to analyze content on social media applications (such as Instagram, yelp, etc.) to identify or estimate ingredients, calories, nutrients, vitamins, etc. The estimate may assume localized ingredients and/or flavors, for example based on weather, season, or religious background.

The meal planning system of any of the preceding paragraphs may also include any combination of the following features described in this paragraph, among others described herein. The meal planning system can further include or communicate with one or more restaurants. A restaurant can communicate information to or from meal planning system, such as to receive the user-specific meal kit, allergies, foods to avoid, etc. Meals based on the user-specific meal kit can be delivered, for example via a delivery service.

Although certain embodiments and examples are disclosed herein, inventive subject matter extends beyond the examples in the specifically disclosed embodiments to other alternative embodiments and/or uses, and to modifications and equivalents thereof.

BRIEF DESCRIPTION OF THE DRAWINGS

Throughout the drawings, reference numbers are re-used to indicate correspondence between referenced elements. The drawings are provided to illustrate embodiments of the subject matter described herein and not to limit the scope thereof.

DETAILED DESCRIPTION OF EMBODIMENTS

Figure 1:
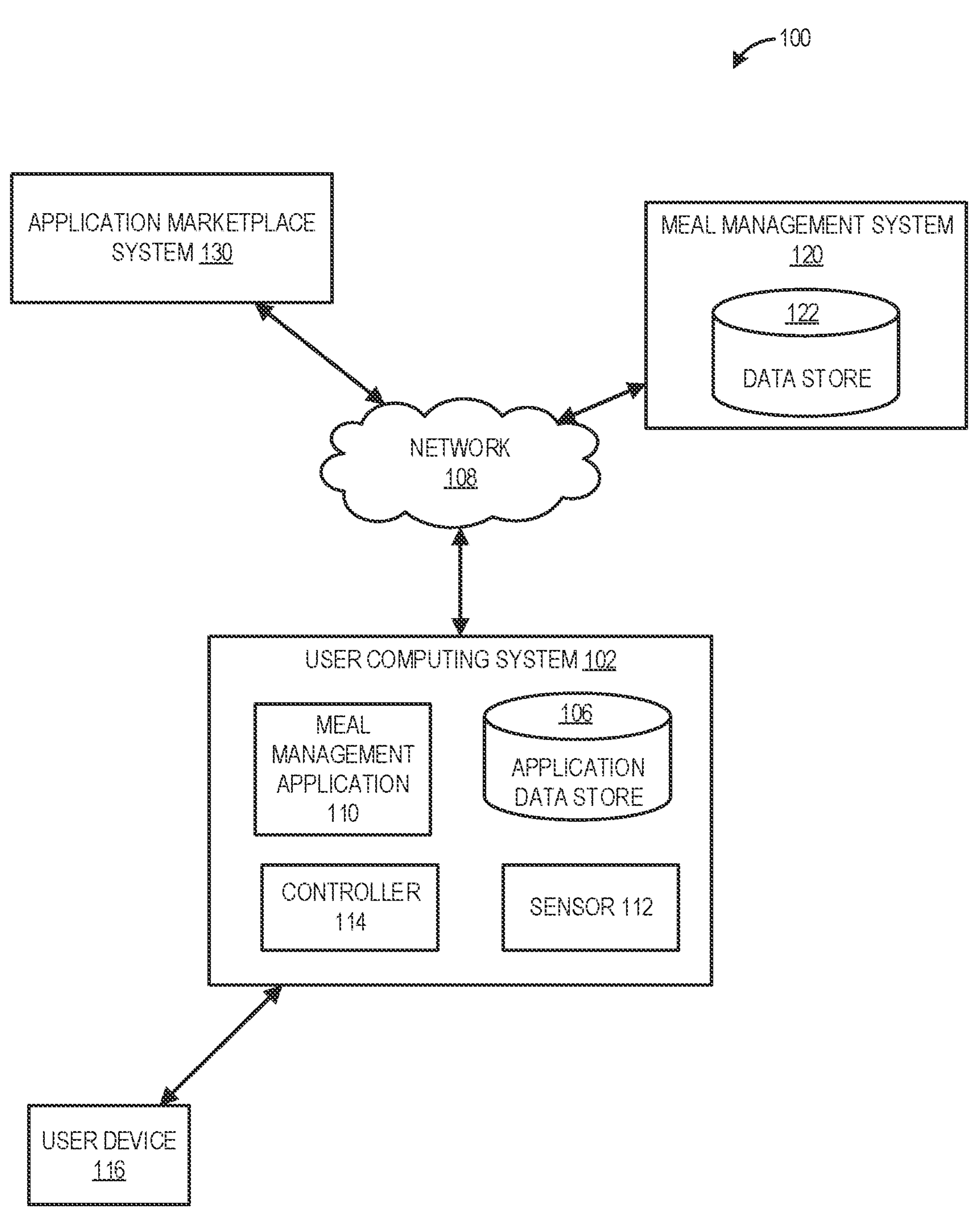
FIG. 1 illustrates an embodiment of a dynamic meal-planning environment.

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

Disclosed is a dynamic meal planning system that generates user-specific meal plans based on data from various different devices and connected technologies that monitor and track various aspects of an individual's daily life. The meal planning system can include a plurality of wearable and/or non-wearable devices, such as those configured with fitness or wellness applications, physiological monitoring capabilities, or food and beverage tracking. In addition, the meal planning system can include or retrieve data from various sensors, such as those related to weather, climate, location, etc. Further still, the meal planning system can access electronic medical records and/or receive user input to obtain data relating to personal medical history, family medical history, food preferences, religion, goals, or other information that may be useful in creating an individualized meal kit for some or all the individual's daily meals.

Disclosed is a meal distribution system that receives and/or modifies the user-specific meal plans and creates the individualized meal kit to provide to the individual. In some cases, the meal distribution system is one or more of a drive thru, an indoor or outdoor restaurant, an indoor or outdoor warehouse kitchen, etc. for users and/or non-users to pick up and/or eat the individualized meal kits. In some cases, the meal distribution system can modify an individualized meal kit based on available ingredients. In some cases, the meal kits may be a meal prep or numerous kits shipped to a user's home or office to be consumed throughout the week. Some or all of the ingredients may be organic and/or sustainably and humanely farmed.

Disclosed is a meal distribution system that generates user-specific meal plans that include at least some foods or ingredients with medicinal properties (sometimes referred to as "food as medicine"). The medical properties may be related to certain health conditions. For example, the medical properties may be related to a current or underlying health condition, a health condition from which the individual has previously recovered, a health condition for which the individual is at risk or a high risk, a health condition that is identified by the individual, etc. The particular health condition can vary across embodiments. For example, the health conditions may relate to a disability, allergy, illness, diseases, habit (for example, smoking), ovulation period, pregnancy, post-pregnancy, family history, medical procedure, etc. Thus, the user-specific meal plans can include or prioritize foods with medicinal properties that may be believed to have a positive effect on the health condition, such as to treat, cure, or reduce the negative side effects of a health condition, or to support the health condition (for example, ovulation period, pregnancy, post-pregnancy, etc.). As a corollary, the user-specific meal plans can exclude or deprioritize foods with properties that may be believed to have a negative effect on the health condition.

In some cases, the user-specific meal plans may include food that may treat, cure, or reduce the negative side effects of a health condition. For example, studies demonstrate that people whose diets are rich in polyphenol antioxidants have lower rates of depression, diabetes, dementia, and heart disease. As such, the user-specific meal plan may prioritize those foods that include antioxidants such as vegetables, fruits, beans, and grains. As another example, the user-specific meal plan may include soup or broth when the individual is sick with the common cold, soft foods after the individual has oral surgery, etc. It will be understood that the particular food as medicine can vary based at least in part on the health condition.

In some cases, the user-specific meal plans may include food that may support the health condition. Consider a scenario in which an individual is attempting to conceive a baby. In some such cases, the meal distribution system may prioritize food choices that are associated with increased fertility (such as sunflower seeds, citrus fruits, mature cheeses, full-fat dairy, liver, cooked tomatoes, beans and lentils, asparagus, etc.) or increased nutrients (such as dairy products, legumes, sweet potatoes, salmon, eggs, broccoli and dark, leafy greens, lean meat and proteins, berries, etc.). In addition, or alternatively, the meal distribution system may avoid foods that may negatively affect fertility or pregnancy, such as those foods that contain toxoplasmosis or *salmonella*, such as raw meat, shellfish, sushi, including oysters, mussels, clams, rare or undercooked beef and poultry, etc.

As another example, consider a scenario in which an individual is a new mother and is nursing. In some such cases, the meal distribution system may prioritize food choices that are associated with boosting breast milk supply, such as fenugreek, oatmeal or oat milk, fennel seeds, lean meat and poultry, garlic, etc. As a corollary, the meal distribution system may refrain from (or limit) using food choices that should generally be avoiding while breastfeeding, such as caffeine, fish, chocolate, dairy products, citrus fruits, wheat/gluten, etc.

Environment Overview

FIG. 1 illustrates an embodiment of a dynamic meal-planning environment 100. The computing environment 100 includes a network 108, a user computing system 102, a user device 116, a meal management system 120, and an application marketplace server 130. To simplify discussion and not to limit the present disclosure, FIG. 1 illustrates only one user computing system 102, one user device 116, one meal management system 120, and one application marketplace server 130, though multiple devices or systems may be used.

Any of the foregoing components or systems of the environment 100 may communicate, such as via the network 108. Although only one network 108 is illustrated, multiple distinct and/or distributed networks 110 may exist. The network 108 can include any type of communication network. For example, the network 108 can include one or more of a wide area network (WAN), a local area network (LAN), a cellular network (e.g., LTE, HSPA, 3G, and other cellular technologies), an ad hoc network, a satellite network, a wired network, a wireless network, Bluetooth, and so forth. In some embodiments, the network 108 can include the Internet. In some cases, two or more of the components or systems of the environment 100 may be connected via a wired connection. In some cases, any one or any combination of the components or systems of the environment 100 may include an Ethernet adapter, cable modem, Wi-Fi adapter, cellular transceiver, baseband processor, Bluetooth or Bluetooth Low Energy (BLE) transceiver, or the like, or a combination thereof.

Any of the foregoing components or systems of the environment 100, such as anyone or any combination of the user computing system 102, the user device 116, the meal management system 120, or the application marketplace server 130 may be implemented using individual computing devices, processors, distributed processing systems, servers, isolated execution environments (e.g., virtual machines, containers, etc.), shared computing resources, or so on. Furthermore, any of the components or systems of the environment 100 may be combined and/or may include software, firmware, hardware, or any combination(s) of software, firmware, or hardware suitable for the purposes described. In some cases, a component or system of the environment 100 can be configured to communicate through another component or system of the environment 100.

The user computing system 102 can be controlled by a user. The user computing system 102 may include hardware and software components for establishing communications over the network 108. For example, the user computing system 102 may be equipped with networking equipment and network software applications (for example, a web browser) that facilitate communications via one or more networks (for example, the Internet or an intranet). The user computing system 102 may have varied local computing resources such as central processing units and architectures, memory, mass storage, graphics processing units, communication network availability and bandwidth, and so forth. Further, the user computing system 102 may include any type of computing system. For example, the user computing system 102 may include any type of computing device(s), such as wearable devices (e.g., smart watches, glasses with computing functionality, etc.), wireless mobile devices (for example, smart phones, PDAs, portable media players, tablets, or the like), laptop computers, desktop computers, gaming devices, car-console devices, and so forth.

The user computing system 102 is capable of executing a meal management application 110, which may be stored and/or executed locally and/or in a distributed environment. The meal management application 110 may include a web browser, a mobile application or "app" available in the application marketplace system 130, a background process that performs various operations with or without direct interaction from a user, or a "plug-in" or "extension" to another application, such as a web browser plug-in or extension.

The meal management application 110 may facilitate dynamic meal planning for one or more individuals. For example, as described herein, the meal management application 110 can communicate with various devices (for example, the user computing system 102, the user device 116) or systems (for example, the meal management system 120) to obtain or track exercise data, meal data, user preference data, health data, or other data. Furthermore, the meal management application 110 can generate a health score based at least in part on the exercise data, the meal data, the user preference data, the health data, and/or the other data. Furthermore, the meal management application 110 can generates user-specific meal plans based at least in part on the health score, the exercise data, the meal data, the user preference data, the health data, and/or the other data. In some cases, the meal management application 110 can receive data, generate a health score, and/or generate user-specific meal plans in real time. A user-specific meal plan (also referred to as a meal kit) can include an indication of one or more foods (for example, a set of foods for a complete meal or snack), an indication of one or more foods, a recipe, among other things.

The meal management application 110 may be configured to receive a scan of a menu or recipe, process the scan to identify one or more meals and/or ingredients of the one or more meals, select at least one of the one or more meals as a suggested meal, and outputting an indication of the suggested meal to the user. For example, the user computing system 102 may include an image capture device, which a user can use to take a picture of the menu and communicate the picture to the meal management application 110 for processing. The suggested meal may be a meal that fits within dietary needs, for example to achieve a particular daily, weekly, or meal score. The suggested meal may be a meal that has a highest health score, as compared to other meals of the menu. To process the scan, the meal management application 110 can analyze content on social media applications (such as Instagram, yelp, etc.) to identify or estimate ingredients, calories, nutrients, vitamins, etc. The estimate may assume localized ingredients and/or flavors, for example based on weather, season, or religious background.

The user computing system 102 can include or communicate with one or more sensors 112. The one or more sensors 112 can vary across embodiments. For example, the one or more sensors 112 can include, but are not limited to, invasive or non-invasive physiological sensors, invasive or non-invasive blood analyte sensors, location tracking devices (for example, GPS), accelerometer, gyroscope, electrodes or one or more photodiodes. Physiological sensors can measure physiological data and can include, but are not limited to, optical sensors, piezoelectric sensors, electrical sensors, biomechanical sensors, temperature sensors, conductance sensors, electrodes or combinations of the same. Physiological parameters can include, but are not limited to, oxygen saturation or $SpO_2$, pulse rate, respiratory rate, pleth variability index (PVI), perfusion index (PI), total hemoglobin or SpHb, methemoglobin or SpMet, carboxyhemoglobin or SpCO, hydration, skin or body temperature, ECG, etc. Blood analyte sensors can measure one or more analytes present in the blood of a user, such as glucose, lipids, hormones, or other analyte. In some cases, the sensor 112 may be configured to administer medications, such as insulin, glucagon, or other medications.

The user computing system 102 may be configured to communicate with one or more hardware processors that may be external to the user computing system 102, such as a cloud-based processor, the user device 116, or other peripheral device. The user computing system 102 may include an NFC tag to support authentication and pairing with a user device 116 or peripheral device, Bluetooth communication with additional user computing systems 102, or Bluetooth communication with a paired user device running an associated control application.

The user device 116 can be controlled by a user. The user device 116 may include any type of computing device(s), such as wearable devices (e.g., smart watches, glasses with computing functionality, etc.), wireless mobile devices (for example, smart phones, PDAs, portable media players, tablets, or the like), laptop computers, desktop computers, gaming devices, car-console devices, and so forth. In some cases, the user device 116 is capable of executing an application, such as the meal management application 110 or other application with which the meal management application 110 or the user computing system 102 can communicate. In some cases, the user device 116 can include a sensor, such as the sensor 112. Furthermore, the user device 116 may include a controller or data store, similar to the controller 114 and application data store 106 of the user computing device.

To support ease of use and safe interaction with the user, the user computing system 102 and/or the user device 116 may incorporate user input through tap-detecting accelerometer or provide feedback via audio speaker, haptic vibration, or optical indicators.

The controller 114 may receive data from the user device 116, user computing system 102, meal management application 110, meal management system 120, etc. and record the data and/or device activity to the application data store 106 and/or the data store 122. In some cases, at the end of the life of a device or system, the controller 114 can be configured to lock operation, and create a data recovery module to permit authenticated access to the recorded data if needed.

The user computing system 102 and/or the user device 116 may include one or more local user interfacing components. For examples, a local user interfacing component may include, but is not limited to one or more optical displays, haptic motors, audio speakers, or user input detectors. In some examples, an optical display may include an LED light configured to display a plurality of colors. In some examples, an optical display may include a digital display of information associated with the user computing system 102 and/or the user device 116, including, but not limited to, device status, medication status, user status, measured analyte or physiological values, the like or a combination thereof. In some examples, a user input detector may include an inertial measurement unit, tap detector, touch display, or other component configured to accept and receive user input. In some examples, audio speakers may be configured to communicate audible alarms related to device status, medication status user status, the like or a combination thereof. A controller may be configured to communicate with the one or more local interfacing components by, for example, receiving user input from one or more user input components or sending control signals to, for example, activate a haptic motor, generate an output to the optical display, generate an audible output, or otherwise control one or more of the local user interfacing components.

The user computing system 102 and/or the user device 116 may include one or more communication components. A communication component can include but is not limited to one or more radios configured to emit Bluetooth, cellular, Wi-Fi, or other wireless signals. In some examples, a communication component can include a port for a wired connection. Additionally, a user computing system 102 and/or user device 116 may include an NFC tag to facilitate in communicating with one or more hardware processors. The one or more communication components and NFC tag may be configured to communicate with the controller 114 in order to send and/or receive information associated with the user computing system 102 and/or the user device 116. For example, a controller 114 may communicate medication information and measured values through the one or more communication components 1140 to an external device. Additionally, the controller 114 may receive instructions associated with measurement sampling rates, medication delivery, or other information associated with operation of any of the components of the computing environment 100 through the one or more communication components from one or more external devices.

The application marketplace server 130 can provide an application marketplace from which the meal management application 110 and/or updates thereto can be communicated to or downloaded by the user computing system 102 and/or the user device 116.

The meal management system 120 can be configured to store data relating to weight management, fitness, wellness, disease prevention, etc. For example, the data store 122 may include a food database that includes nutritional information regarding various food, a fitness database that includes information regarding various workouts, etc. In some implementations, the data store 122 can be configured to store or access information related to admissions, discharges, transfers, etc. of patients such as, but not limited to, patient name, birth date, height, weight, medical history, health issues, allergies, prescriptions, treatments, drug administrations, social security number, admissions, discharges, transfers, etc. In some implementations, the data store 122 can be configured to store electronic medical records (EMRs). The meal management system 120 can communicate with the user computing system 102. For example, the meal management system 120 can obtain updates when a user adds foods in the meal management application 110. As another example, the meal management application 110 can obtain information from the meal management system 120, such a nutritional information relating to certain foods.

Figure 2:
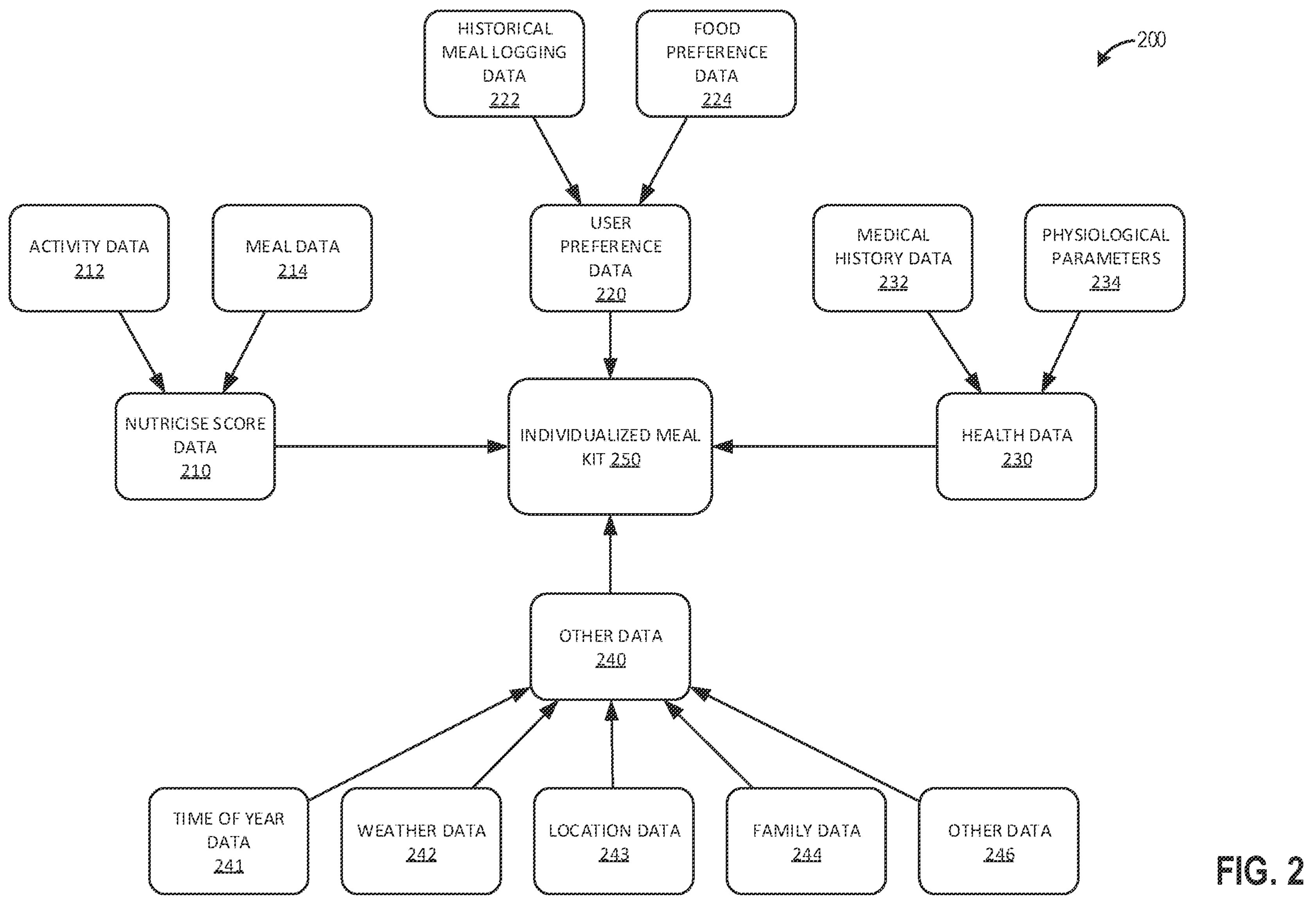
FIG. 2 is an example data flow diagram illustrating types of data used to generate an individualized meal kit.

FIG. 2 is an example data flow diagram 200 illustrating types of data used to generate an individualized meal kit. As indicated by the data flow diagram 200, a user-specific meal plan can be generated based on various types of data including, but not limited to, a health score 210, user preference data 220, health data 230, and other data 240.

The health score 210 can provide an overall indication of the nutritional completeness of a particular food, beverage, meal, or set of meals. In some cases, a health score is generated for a prospective food, beverage, meal, or set of meals. In this way, the health score can be usable to identify a "what if I eat it" scenario. In some cases, a health score is generated for a past food, beverage, meal, or set of meals. In this way, the health score can indicate a progress or report card indication of past nutritional completeness over a particular period of time.

The health score 210 can be generated based on a number of inputs. For example, in some cases, the health score 210 can be generated based at least in part on activity data 212 and meal data 214. The activity data 212 can vary across embodiments. For example, the activity data 212 can include, but is not limited to, fitness-related metrics such as distance walked or run, calories burned, active calories, distance, active time, type of exercise, exercise history, exercise plan, fitness goals, etc. The meal data 214 can vary across embodiments. For example, the meal data 214 can include, but is not limited to, food or beverage intake-related metrics such as calories consumed, carbohydrate quantity, food type, macronutrients, micronutrients, carbohydrate type, glycemic indexes, timing of intake, ingredients such as caffeine, alcohol, hydration status, etc.

The activity data 212 can be generated from sensor data, user-inputted data, or a health data repository, for example. Such sensor data may include accelerometers, gyroscopes, altimeters, thermistors, pulse oximeters, continuous glucose monitors, blood analyte monitors, etc. Each sensor may detect certain types of activities but may be unable to detect other types of activities, depending on their location of placement, their inherent accuracies, or the limitations of the technology. For example, an accelerometer placed on the abdomen may not easily detect arm and hand movement, but an accelerometer placed on the wrist may have a higher chance of detecting various arm and hand movements. Additionally, various activities may trigger different energy systems in the body, such as aerobic and anaerobic exercises. However, a combination of multiple sensors may help identify gaps in activities. For example, certain vigorous and/or intense activities, such as weightlifting, may be detectable with a pulse oximeter due to the elevated pulse rate and lower oxygen levels. The combination of one or more sensors may help to identify the activity type, which may help compute the activity data 212. The health score 210 may be defined with the equation below:

health score=function(activity data)+function(meal data)

Once the activity type is determined, a conversion into an activity measure may be computed to assist in calculating the activity data 212. Depending on the activity type, a compendium of exercises may be utilized to convert from activities to metabolic expenditure, also known as metabolic equivalent of task (MET). This conversion may allow different activities of various types to be compared on the same or similar relative scale. Finally, this activity measure may be personalized for the user. For example, the activity measure can account for the age, weight, gender, and basal metabolic rate of the user to contribute into the health score 210. The activity data may be defined with the equation below:

activity data=function(activity type,duration,intensity, METs,pulse rate,$SpO_2$)

The meal data 214 represents an overall assessment of quantity and quality of the meal. The quantity of the meal may be captured by the calories present in the food, which can be provided by the mass of macronutrients (e.g., carbohydrates, proteins, and fat) present in the meal. The quality of the meal can take into account the daily recommended values for the intake of macronutrients and micronutrients (e.g., fiber, sodium, added sugars, vitamins, minerals, etc.). Based on scientific evidence and FDA guidelines for healthy eating, each nutrient may have a recommended amount as well as a series of consequences based on the amount of excess or deficiency of each nutrient. The score can be adjusted to reflect the impact of the nutrients on the user's health based on their consumption of food and how they contribute to the risks for cardiovascular disease, obesity, diabetes, CoPD, possible complications, death, etc. For example, excess intake of sodium can be associated with higher systolic blood pressure and hence a higher incidence of cardiovascular disease. However, excess intake of fiber can be associated with lower systolic blood pressure. By providing a weighted combination of the nutritional facts, each meal can be summarized for a user to promote the consumption of healthy foods and to discourage consumption of unhealthy foods. The meal data 214 may be defined with the equation below:

meal data=function(macronutrients,micronutrients)

The meal data 214 can be personalized for a user by adjusting meal combinations based on motivation. In some instances, a user with prediabetes may be primarily concerned about weight loss, and hence a primary target will be to reduce caloric intake to achieve that goal. For example, if a user requires 2000 calories to maintain his/her weight, then the target may be lowered to possibly 1500 calories to help the user achieve the user's goal for 6-7% weight loss. However, a healthy individual may be concerned more about the quality of the food and may aim to achieve the daily recommended limits for the macronutrients and micronutrients. The meal kit may be adjusted based on the user's motivation and adjusted to maintain the recommended balance. An optimization routine may be executed to compute the combination of different meals for breakfast, lunch, and dinner, which would allow the user to meet his/her target needs for the day.

The user preference data 220 can include, but is not limited to, historical meal logging data 222 and food preference data 224. Historical meal logging data 222 can include, but is not limited to, a history of past meal data 214 (including meals already consumed that day), the frequency at which the user logs or fails to log meals, etc. Food preference data 224 can include, but is not limited to, food preferences related to taste preferences, religion (for example, veganism), social justice (for example, vegetarianism), underlying health conditions (for example, diabetes, heart problems, rheumatoid arteritis, liver disease, kidney disease, Alzheimer, asthma), preferred diet (for example, locally grown, organic, sustainably and humanely farmed, etc.), foods to avoid (e.g., red meat), etc. For example, with respect to underlying health conditions, the user may indicate a preference for foods that have been shown (for example, anecdotally, scientifically, etc.) to help with the underlying health condition. For example, an individual with a family history of Alzheimer's disease may prefer foods that can fight off cognitive decline, such as leafy greens, berries, nuts, etc. Accordingly, in some cases, the individualized meal kit can include food that is seen as a medicine for certain diseases.

The health data 230 can include, but is not limited to, medical history data 232 and physiological parameters 234. The medical history data 232 can include, but is not limited to, information relating to health conditions (for example, pregnant, trying to conceive, breastfeeding, etc.), habits (for example, smoking, drinking, drugs, etc.), allergies, illnesses, diseases, prescriptions or other medications, surgeries, immunizations, results of physical exams and tests, family medical history, age, weight, etc. The physiological parameters 234 can include real-time or non-real-time physiological data including, but not limited to, oxygen saturation or $SpO_2$, pulse rate, respiratory rate, pleth variability index (PVI), perfusion index (PI), total hemoglobin or SpHb, methemoglobin or SpMet, carboxyhemoglobin or SpCO, hydration, skin or body temperature, or analytes present in the blood of a user, such as glucose, lipids, hormones, or other analyte.

The other data 240 can include, but is not limited to, time of year data 241, weather data, location data 243, family data 244, or other data 245. The time of year data 241 can include information relating the date, month, year, season, hour, minutes, day of the week, etc. Weather data can include information relating to the state of the atmosphere, including temperature, wind speed, rain or snow, humidity, pressure, etc. Location data 243 can include a location of the user, such as the GPS coordinates, city, state, region, etc. Family data 244 can include, but is not limited to, family dynamic or health score 210, user preference data 220, or health data 230 of another person, such as a personal with whom the individual may be sharing the meal. For example, in some cases, the individualized meal kit may be modified such that the meal kit is individualized for a group of people (for example, a family) rather than a single person. In this way, the food of the meal kit may be shared amongst a group and require less of a burden to make, as compared to individual meals for each person. Other data 243 can include any other data that may be considered when generating the individualized meal kit.

The individualized meal kit can be generated based on the various types of data. In some cases, individualized meal kits are generated daily, weekly, or per meal. The individualized meal kits can be dynamically modified such that data received in real time can affect the contents of the individualized meal kit. In some cases, the individualized meal kit can provide intraday customizations. For example, the content of an individualized meal kit generated for a lunch meal may be influenced by the content of the breakfast that the individual had that day.

In some cases, some of the information that is used to generate the individualized meal kit may be estimated information. For example, if the user input a meal or food, the exact ingredients may be unknown. In some such cases, the system may estimate ingredients/recipe and/or assume that the recipe is using localized ingredients and/or flavors. For example, based on a user living in Tennessee and inputting barbeque ribs as a food input, the system can assume a Tennessee barbeque sauce rather than a Texas barbeque sauce.

Figure 3:
FIG. 3 is a flow diagram illustrative of an example of a routine implemented by a meal-planning system for generating an individualized meal kit.
Figure 3:
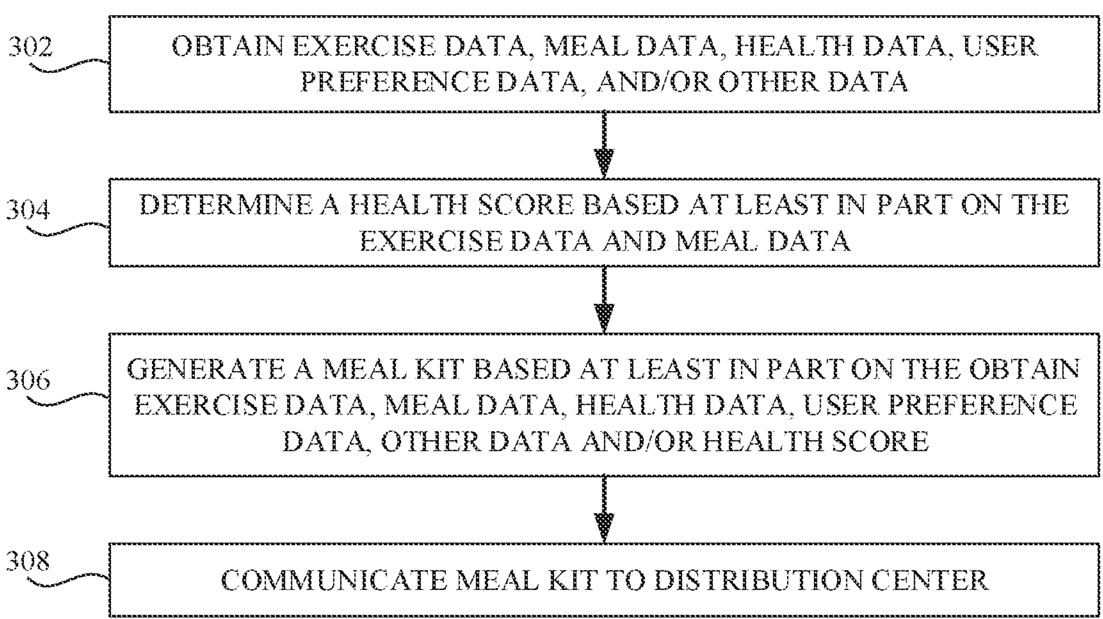

FIG. 3 is a flow diagram illustrative of an example of a routine 300 implemented by a meal-planning system for generating an individualized meal kit. Although described as being implemented by a meal-planning system, it will be understood that one or more elements outlined for routine 300 can be implemented by one or more computing devices or components that are associated with the dynamic meal-planning environment 100, such as, but not limited to, the user computing system 102, the user device 116, the meal management system 120, and/or the meal management application 110. Thus, the following illustrative embodiment should not be construed as limiting.

At block 302, as described herein, the meal-planning system obtains exercise data, meal data, health data, user preference data, and/or other data.

At block 304, as described herein, the meal-planning system determines a health score based at least in part on the exercise data, the meal data, the health data, the user preference data, and/or the other data.

At block 306, the meal-planning system generates a meal kit based at least in part on the health score, the exercise data, the meal data, the health data, the user preference data, and/or the other data.

At block 308, the meal-planning system communicates the meal kit. In some cases, the meal-planning system communicates the meal kit to the individual for which the meal kit was generated. For example, the meal kit may include a list of ingredients and/or recipe that can or must be cooked by hand, such as by the individual. For example, the meal kit may be downloadable to the user computing system 102 or viewable via the meal management application 110.

In some cases, the meal-planning system communicates the meal kit to a distribution center. In turn, the distribution center can provide an ingredient-and-recipe service for the individual based on the meal kit. Alternatively, in some cases, the distribution center can prepare the meal according to the meal kit and provide the prepare meal to the individual. In some cases, the meal distribution system is one or more of a drive thru, an indoor or outdoor restaurant, an indoor or outdoor warehouse kitchen, etc. for users and/or non-users to pick up and/or eat the individualized meal kits. In some cases, the meal distribution system can modify an individualized meal kit based on available ingredients.

Fewer, more, or different blocks can be used as part of the routine 300. In some cases, one or more blocks can be omitted. In some embodiments, the blocks of the routine 300 can be combined with any one or more of any other blocks.

Smart Food Tray

Figure 4:
FIG. 4 illustrates an example smart food tray.
Figure 4:
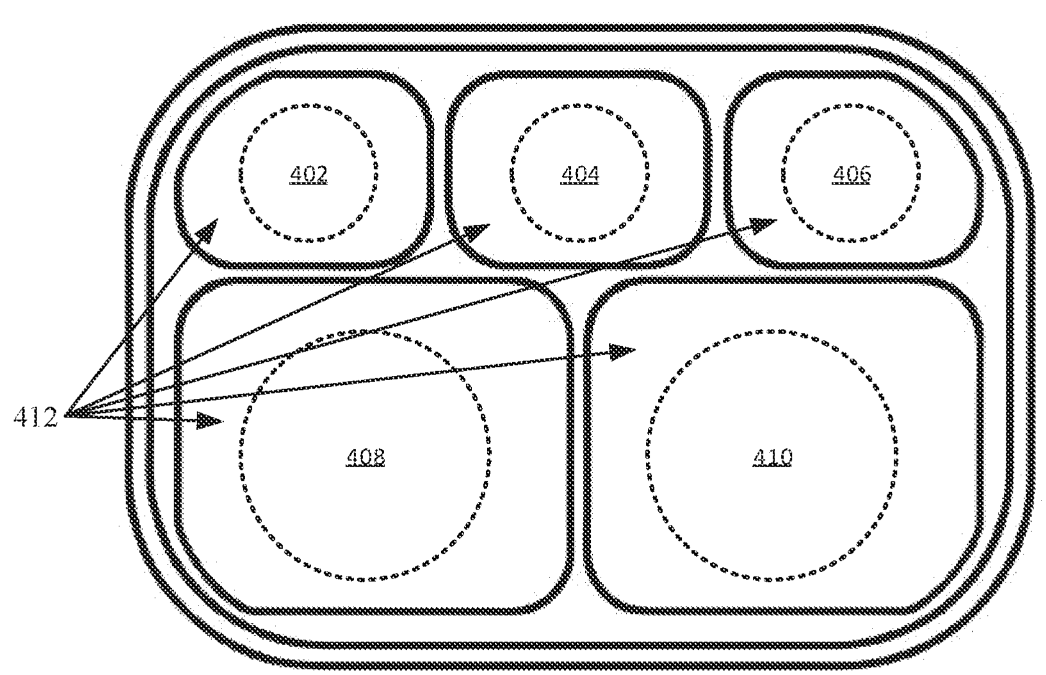

FIG. 4 illustrates an example smart food tray 400. A food scale can aid a user in monitoring or measuring the weight of their food, their carbohydrate quantity, food type, macronutrients, micronutrients, carbohydrate type, glycemic indexes, timing of intake, etc. The tray 400 can include a flat dish or container for use in carrying, serving, holding, or eating food.

As illustrated, the tray 400 can include one, or a plurality of compartments 412 to place food. The tray 400 may include one or more integrated scales for weighing food. In the illustrated embodiment, the tray 400 includes a separate scale 402, 404, 406, 408, 410 for each compartment 412. In this way, the tray 400 may be able to determine or monitor the weight (for example, in ounces), size (for example, in servings), timing, etc. of each of the different food items placed in the different compartments 412. In additional or alternatively, the tray 400 can include a different number of integrated scales and/or position them differently across the tray 400.

In some cases, the tray 400 may be able to determine what and how much of each sub compartment the person is consuming, for example, based on their pace of eating. For example, the tray 400 may be able to track the order in which foods were consumed, the pace in which foods were consumed, timing details associated with the meal, etc. In some cases, the tray 400 can track this information in real time. In some cases, the tray 400 may be able to communicate this information to one or more devices or systems, such as over a network.

In some cases, the tray 400 may contain one or more cameras spaced around the tray to aid in identifying the food. The cameras may be black and white, color, infrared, LIDAR, ambient sensors, or the like, and may include LEDs for lighting in dark environments. In some situations, the user may be allowed to fill the tray with food that the user has prepared. Hence, the system may require these additional cameras to capture images and/or videos of the food as it is loaded onto the tray and consumed by the user. The system may employ various image and/or video processing techniques to determine the type of food, the ingredients contained, the cuisine of food, the presence or absence of allergens, the rate of consumption. Such processing techniques include but are not limited to edge detection, image segmentation, object localization, object tracking, image classification, neural networks, deep learning techniques, etc. In some instances, the food may be prepackaged, and a camera may aid in scanning a barcode or QR code, which may identify the food as programmed in the database.

In some cases, the tray 400 may include sensors to detect when the food package is opened. For example, the food may be packaged containing high concentrations of nitrogen to ensure that the food may stay fresher longer. When the package is opened, the nitrogen gas may be picked up by the gas sensor. This trigger may allow the tray to notify the app through various communication methods and aid in logging that the food is currently being consumed or soon to be consumed.

In some cases, the tray 400 may contain heating elements to aid in warming up the food. These heating elements may help keep the food warm in transit from a preparation facility to the place of consumption. For example, the food may be prepared in a hospital, prison, cafeteria, and the food may be delivered to patient, inmate, or student. The food may also be stored by a user in the refrigerator at a school or a workplace, and the heating element in the tray may aid in warming up the food prior to consumption. In some instances, each compartment may require different amounts of heating because each compartment can contain different food items. For example, carbohydrates and proteins may need to be cooked longer, but an uncooked salad may not be heated at all. The heating elements may be composed of induction heaters, electric heaters, or phase-change materials.

The tray 400 can be made of a variety of different materials depending on the embodiment. For example, the tray 400 can be made of any combination of one or more of wood, silver or other metal, plastic, etc. In some cases, the tray 400 is disposable or recyclable.

Although the embodiment of FIG. 4 is described with reference to a food tray, it will be understood that similar techniques can be utilized for other food or beverage containers. For example, one or more scales can be combined with a plate, bowl, cup, mug, refrigerator drawer or shelf, pantry drawer or shelf, cooking pan, etc.

What is claimed is:

1. A system for dynamic meal planning, the system comprising:
- a plurality of sensors configured to measure a plurality of physiological data, the sensors including at least an accelerometer, a gyroscope, an altimeter, a pulse rate sensor, and a thermistor;
- a user device;
- a smart food tray comprising one or more scales configured to measure a weight of a user's food and one or more cameras configured to image the user's food; and
- one or more processors configured to:
  - receive a signal from the smart food tray, the signal indicative of the weight of the food the user consumes and indicative of the imaging by the one or more cameras;
  - determine a type and quantity of food consumed based at least in part on the imaging by the one or more cameras and the weight measured by the one or more scales;
  - receive sensor information from the plurality of sensors, determine an activity type based on the sensor information, determine a metabolic equivalent task (MET) for the activity type and determine activity data based at least in part on the activity type, duration, intensity, and the MET;
  - determine a health score based at least in part on the activity data and the type and quantity of food consumed, and adjusting the health score based on nutrients consumed as determined by the determined type of food;

communicate, to the user device, a prospective health score based on a plurality of prospective food options in order to promote consumption of healthy foods;

dynamically adjusting, in real time, contents of an individualized meal kit based on the determined type of food.

2. The system of claim 1, wherein the system is further configured to dynamically adjust contents of an individualized meal kit based on physiological data.

3. The system of claim 1, further comprising dynamically adjusting contents of an individualized meal kit based on a plurality of food preference data.

4. The system of claim 1, wherein the one or more cameras are configured to scan a barcode of a food package of the user's food.

5. The system of claim 1, wherein the smart food tray comprises a plurality of cameras spaced around the smart food tray.

6. The system of claim 1, wherein the smart food tray comprises a heating element configured to warm food on the smart food tray.

7. The system of claim 1, wherein the one or more processors are configured to track a pace of food consumption based at least in part on the signal from the smart food tray.

8. A method for dynamic meal planning, the method comprising:

receiving by one or more processors a signal from a smart food tray comprising one or more scales configured to measure a weight of a user's food and one or more cameras configured to image the user's food, the signal indicative of the weight of the food the user consumes and indicative of the imaging by the one or more cameras;

determining a type and quantity of food consumed based at least in part on the imaging by the one or more cameras and the weight of the food from the one or more scales;

receiving sensor information from a plurality of sensors, determine an activity type based on the sensor information, determine a metabolic equivalent task (MET) for the activity type and determine activity data based at least in part on the activity type, duration, intensity, and the MET, the sensors including at least an accelerometer, a gyroscope, an altimeter, a pulse rate sensor, and a thermistor;

determining a health score based at least in part on the activity data and the type and quantity of food consumed, and adjusting the health score based on nutrients consumed as determined by the determined type of food;

communicating, to a user device, a prospective health score based on a plurality of prospective food options in order to promote consumption of healthy foods;

dynamically adjusting, in real time, contents of an individualized meal kit based on the determined type of food.

9. The method of claim 8, further comprising dynamically adjusting the meal kit based on physiological data.

10. The method of claim 8, further comprising dynamically adjusting contents of an individualized meal kit based on a plurality of food preference data.

11. The method of claim 8, comprising, using one of the one or more cameras of the smart food tray, scanning a barcode of a food package of the user's food.

12. The method of claim 8, comprising, using a heating element of the smart food tray, warming food on the smart food tray.

13. The method of claim 8, comprising tracking a pace of food consumption based at least in part on the signal from the smart food tray.

* * * * *